(12) United States Patent
Vedrine et al.

(10) Patent No.: US 7,681,570 B2
(45) Date of Patent: Mar. 23, 2010

(54) SPRAY DEVICE OR INJECTION DEVICE ENABLING DELIVERY OF AT LEAST TWO PREDETERMINED PRODUCT DOSES

(75) Inventors: Lionel Vedrine, Ridgewood, NJ (US); Frederic Perot, Saint Paul de Varces (FR); Laurent Barrelle, Saint Nizier du Moucherotte (FR)

(73) Assignee: Becton Dickinson France S.A.S., Pont de Claix (FR)

( * ) Notice: Subject to any disclaimer, the term of this patent is extended or adjusted under 35 U.S.C. 154(b) by 1194 days.

(21) Appl. No.: 10/529,050

(22) PCT Filed: Sep. 26, 2003

(86) PCT No.: PCT/FR03/02836

§ 371 (c)(1),
(2), (4) Date: Oct. 5, 2005

(87) PCT Pub. No.: WO2004/028703

PCT Pub. Date: Apr. 8, 2004

(65) Prior Publication Data

US 2006/0124778 A1   Jun. 15, 2006

(30) Foreign Application Priority Data

Sep. 27, 2002   (FR) ................................. 02 12002

(51) Int. Cl.
*B05B 7/00*   (2006.01)
*B05B 11/00*   (2006.01)

(52) U.S. Cl. ............................ 128/200.19; 128/200.14; 128/200.17; 128/207.18; 604/208; 604/220; 604/234

(58) Field of Classification Search ............ 128/200.14, 128/200.17, 200.19, 207.18; 604/208, 220, 604/234
See application file for complete search history.

(56) References Cited

U.S. PATENT DOCUMENTS

| | | | | |
|---|---|---|---|---|
| 2,648,334 A * | 8/1953 | Brown et al. | ................. | 604/205 |
| 4,583,978 A * | 4/1986 | Porat et al. | .................. | 604/208 |
| 4,929,230 A * | 5/1990 | Pfleger | ......................... | 604/90 |
| 4,962,868 A * | 10/1990 | Borchard | ...................... | 222/49 |
| 5,427,280 A * | 6/1995 | Fuchs | ........................... | 222/320 |
| 5,601,077 A * | 2/1997 | Imbert | .................... | 128/200.14 |
| 5,951,526 A * | 9/1999 | Korisch et al. | .............. | 604/208 |
| 6,382,465 B1 * | 5/2002 | Greiner-Perth | ................ | 222/82 |

FOREIGN PATENT DOCUMENTS

EP         1129786 A2 *   9/2001

* cited by examiner

*Primary Examiner*—Justine R Yu
*Assistant Examiner*—Clinton Ostrup
(74) *Attorney, Agent, or Firm*—David M. Fortunato; Cohen, Pontani, Lieberman & Pavane LLP

(57) ABSTRACT

A spray or injection device that includes a casing or a pusher that includes at least one tab configured to move radially between a first radial position in which the tab does not impede the movement of the pusher with respect to the casing, and a second radial position in which the tab opposes movement of the pusher. The tab includes an opening. The pusher or the casing, respectively, includes at least one ramp-shaped projection configured to bring the tab into the second radial position then to penetrate the opening thereby allowing the tab to return to the first radial position. The pusher or the casing, respectively, further includes at least one stop region against which the tab abuts when the tab is brought into the second radial position by the projection. The stop region occurring just before the projection being opposite the opening.

13 Claims, 14 Drawing Sheets

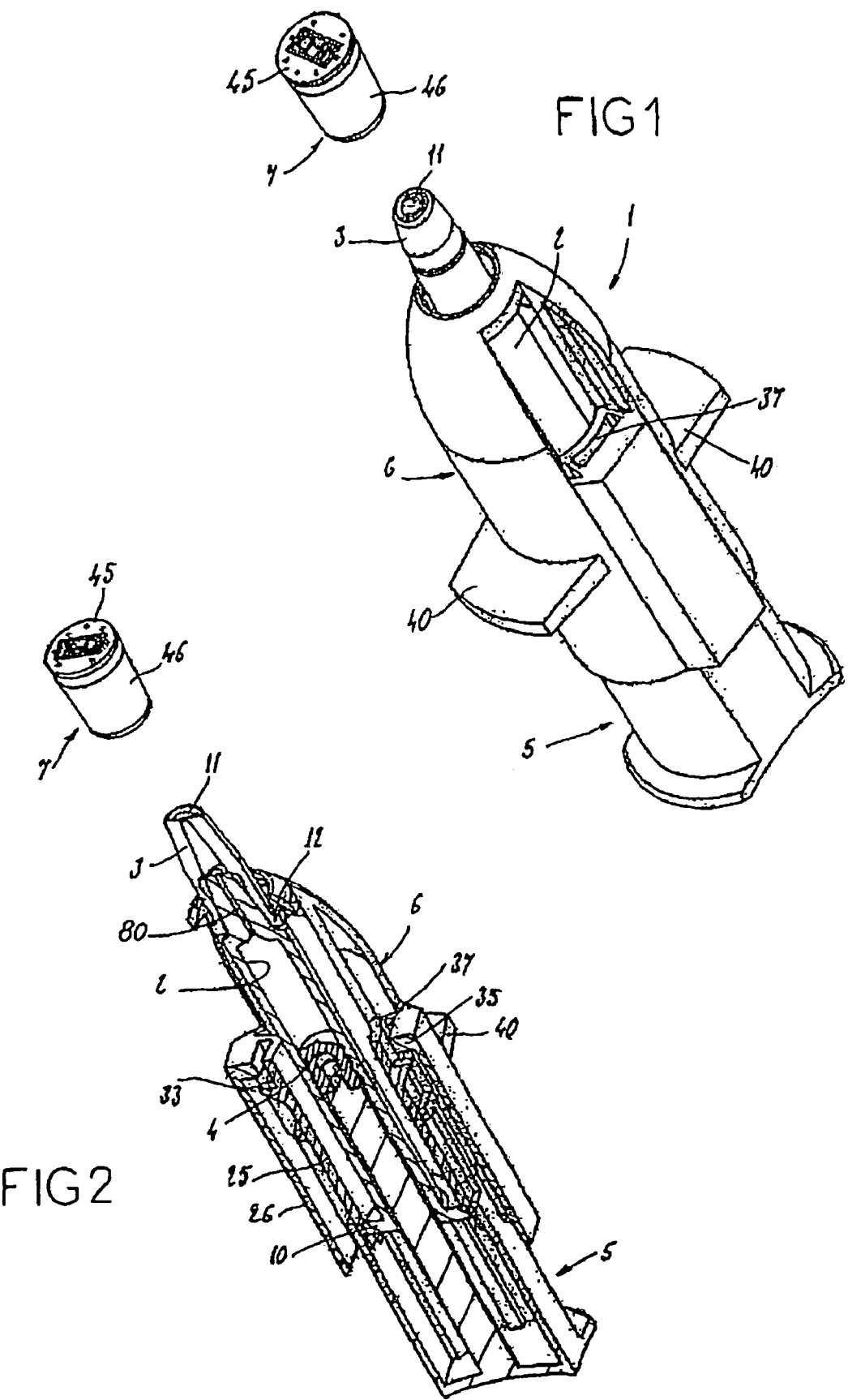

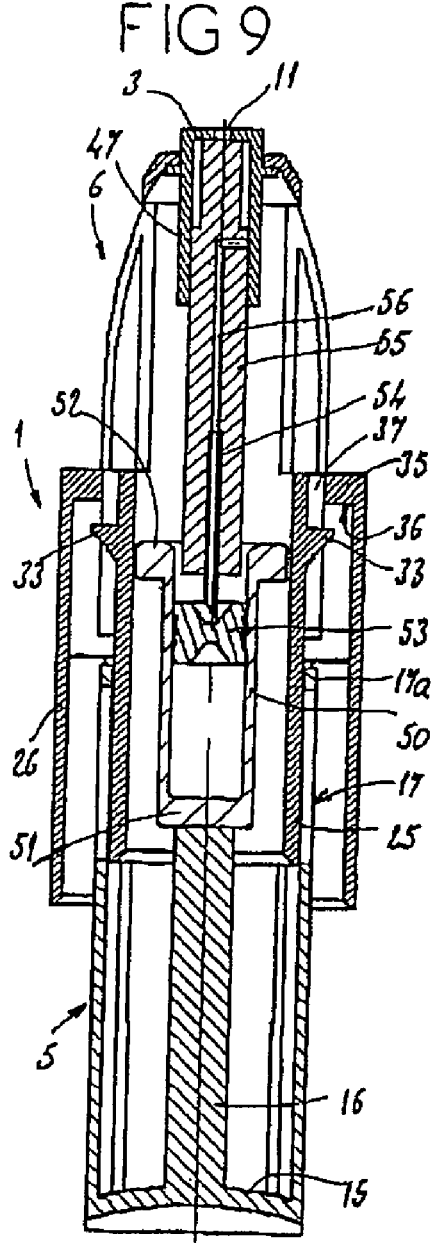
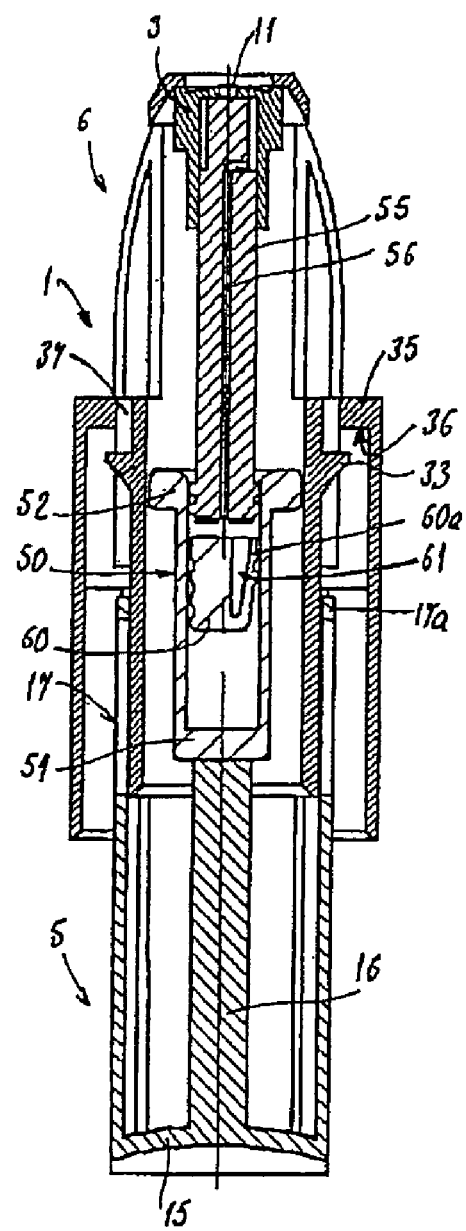

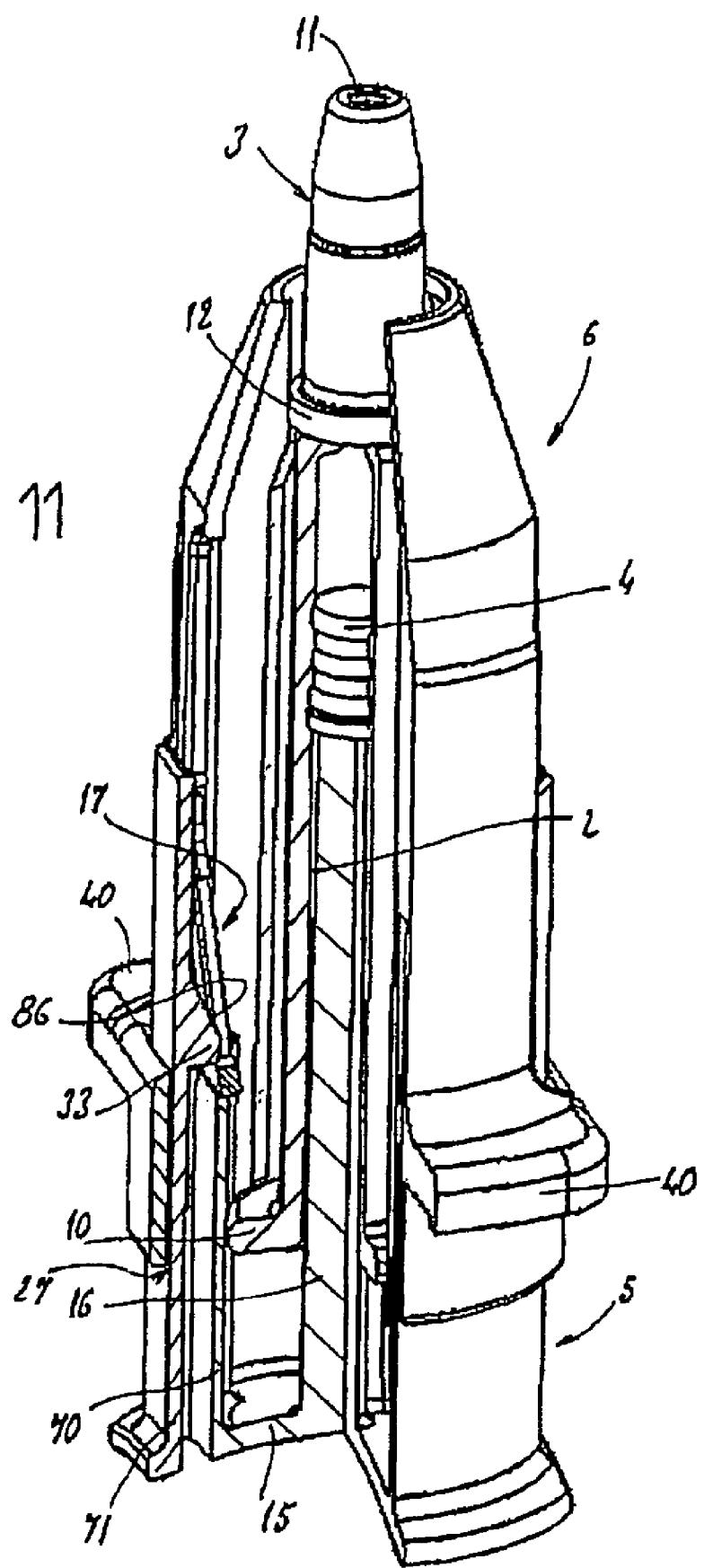

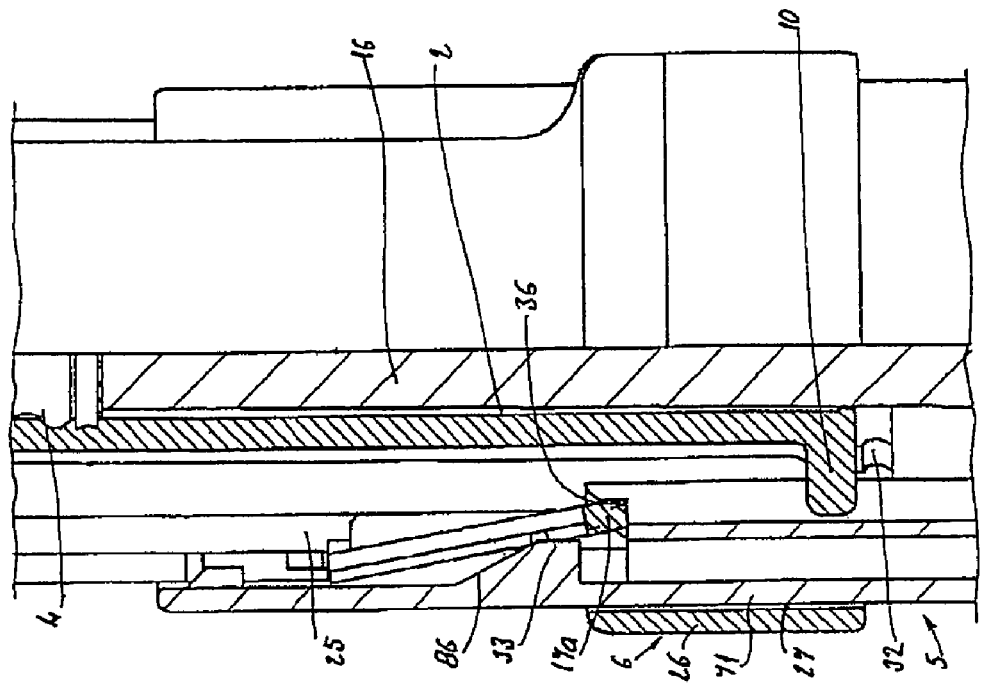
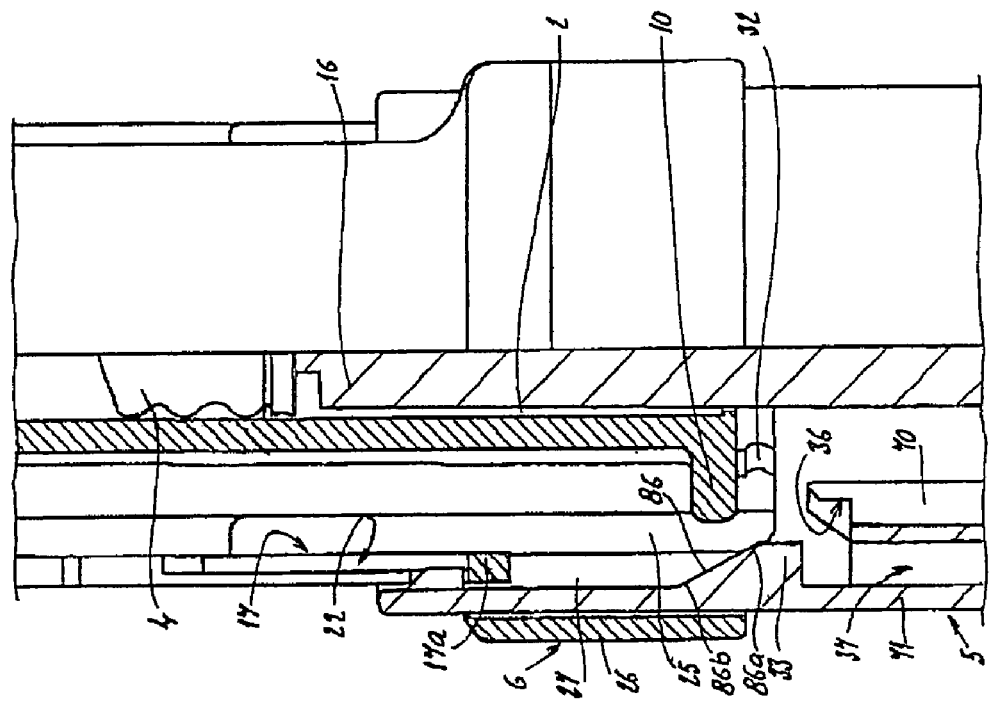

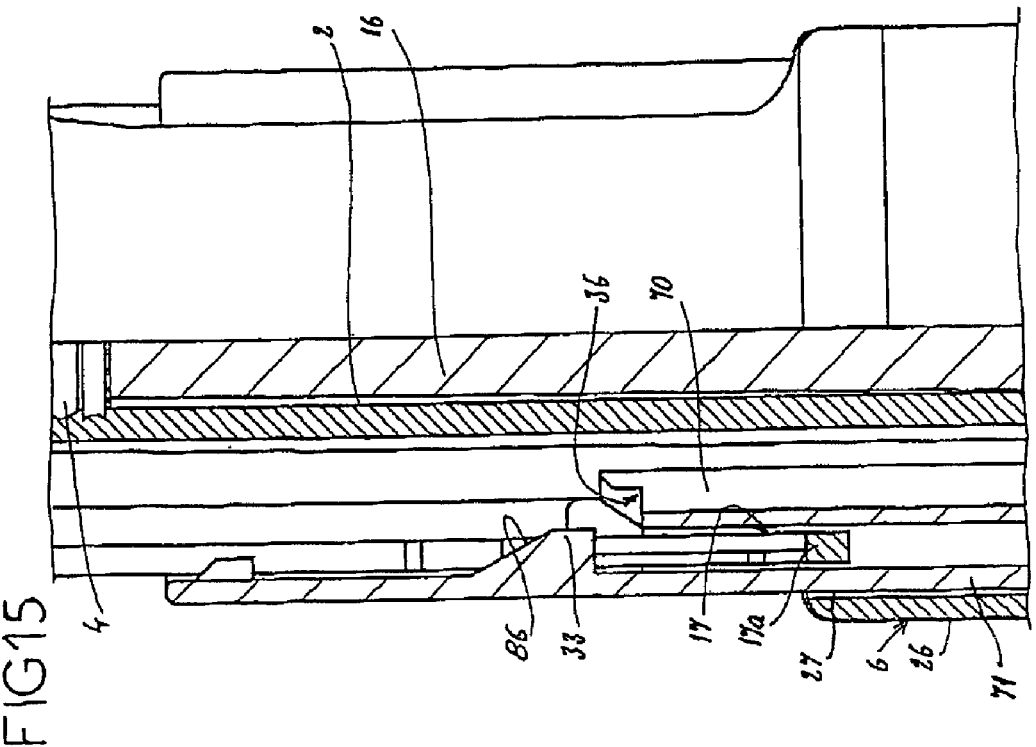
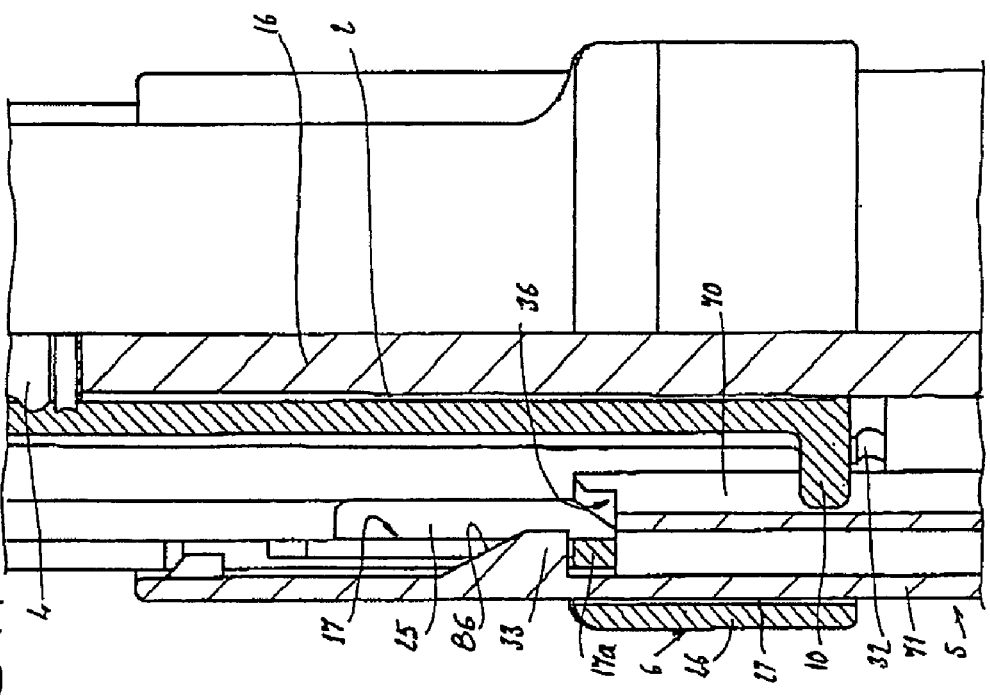

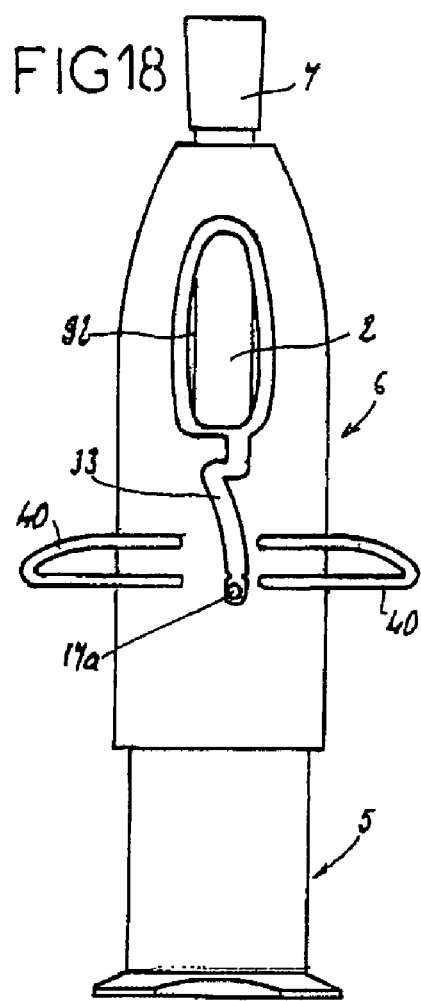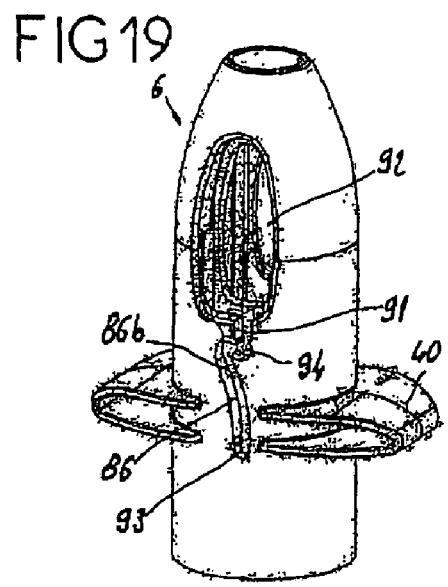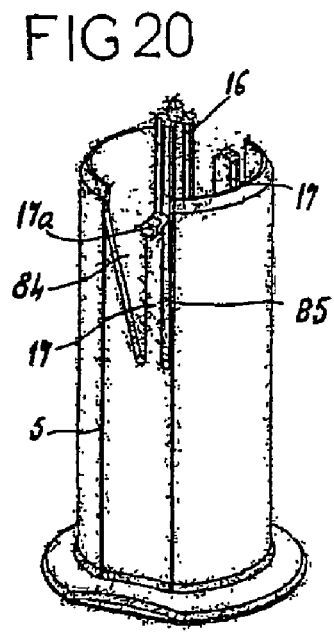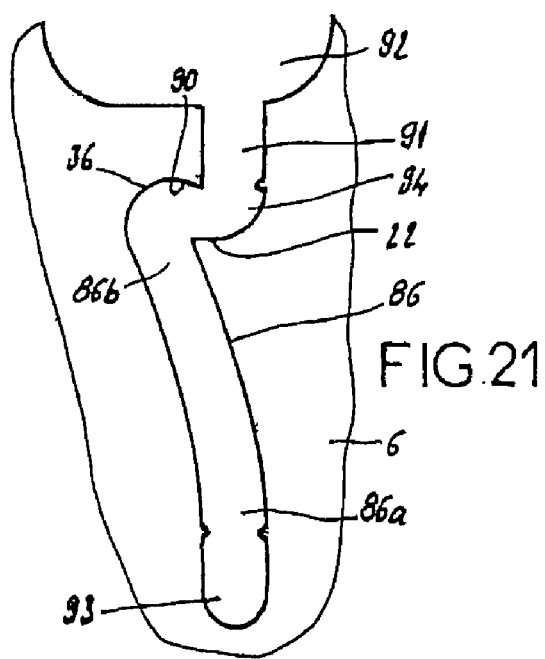

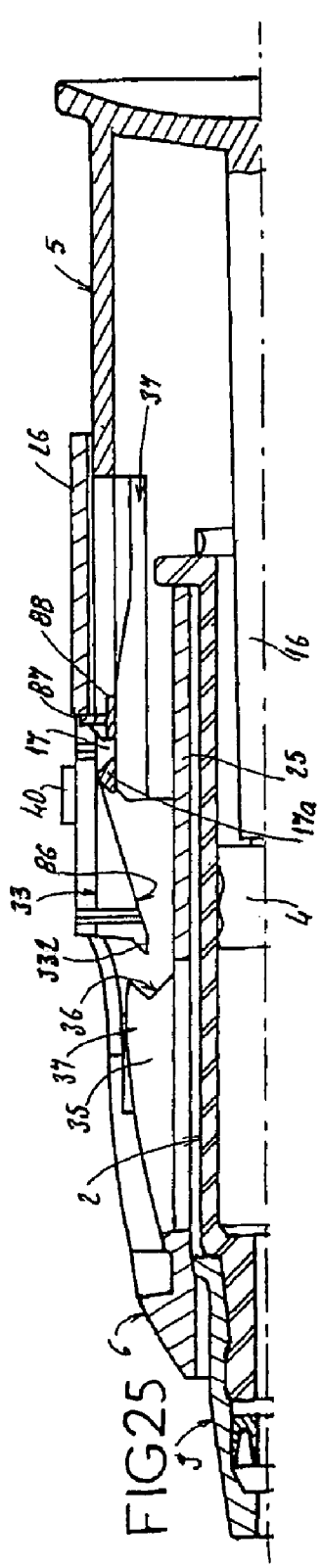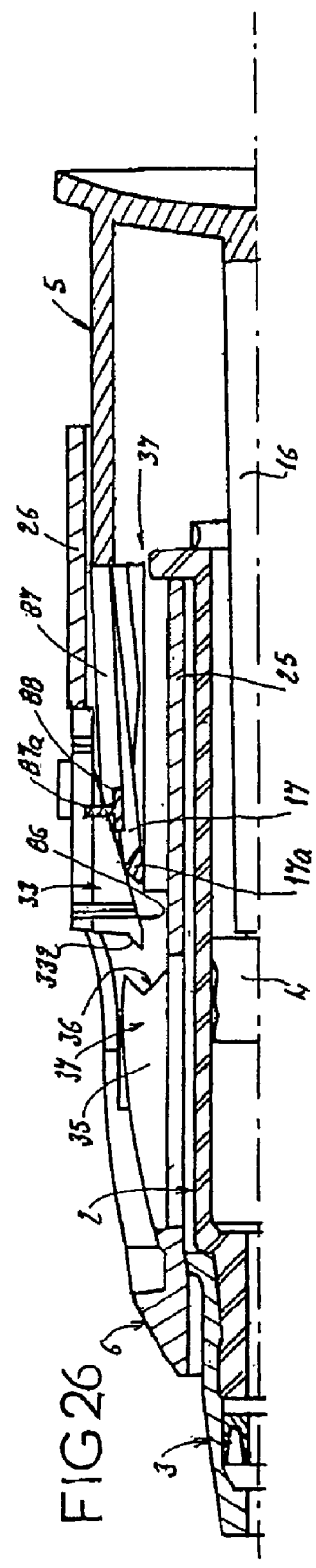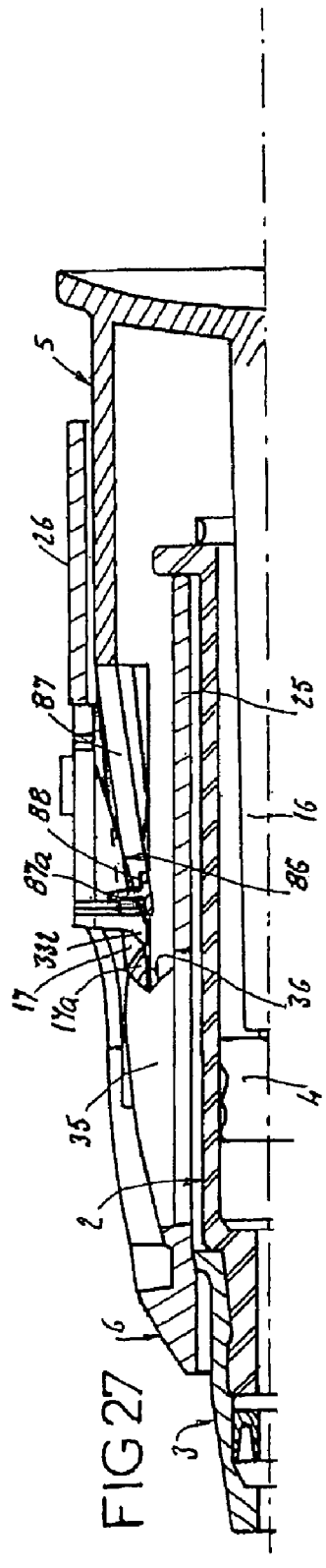

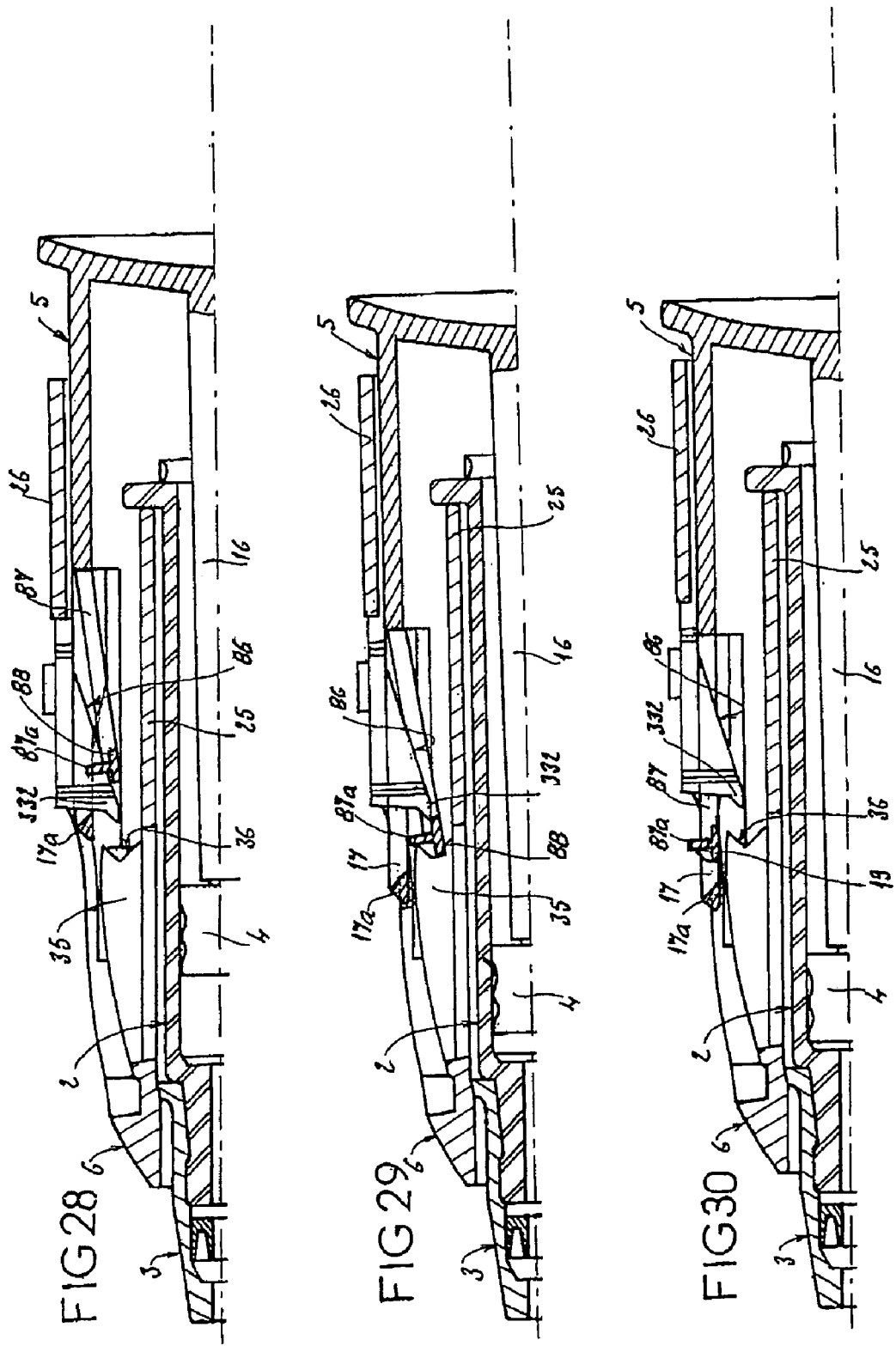

SPRAY DEVICE OR INJECTION DEVICE ENABLING DELIVERY OF AT LEAST TWO PREDETERMINED PRODUCT DOSES

The present invention relates to a spray or injection device for spraying or injecting a product of interest in liquid form, making it possible to deliver at least a first dose and a second dose of said product in succession. The invention is especially applicable to a nasal spray making it possible to deliver two doses, one for each nostril.

It is known to produce a nasal spray based on the general structure of a syringe, comprising detachable stop means. These stop means make it possible, when they are in place, to define a portion of travel of the plunger rod, in order to deliver a first dose, and may be withdrawn or removed in order to free the rest of the travel of the plunger rod, to allow the delivery of the second dose. U.S. Pat. Nos. 5,601,077 and 5,951,526, in the name of the Applicant, illustrate this technique.

U.S. Pat. No. 6,382,204, also in the name of the Applicant, also discloses the producing of a device comprising a casing receiving the syringe body and a pusher forming the plunger rod, the casing comprising lugs and the pusher comprising grooves in which these lugs can slide. Each groove comprises two longitudinal portions offset at an angle and an intermediate portion connecting these two longitudinal portions, perpendicular to the axis of the pusher. Each lug is able to slide in a first longitudinal portion until it comes into abutment against the pusher in the region for connecting this first longitudinal portion to the intermediate portion then, by axial rotation of the pusher, take the intermediate portion until it comes opposite the second longitudinal portion, and then slide in this second longitudinal portion. Said longitudinal portions thus define two successive portions of travel of the pusher, determining the delivery of the first and second doses of product, respectively.

The existing devices have the drawback of not being very easy to manipulate, whether in terms of removing said stop means according to the first technique cited or in terms of performing the relative pivoting of the pusher and of the casing according to the second technique cited.

These devices also have the drawback of not preventing errors in use.

Furthermore, the design of the aforementioned grooves and lugs is relatively complex to achieve in order to obtain good operational reliability.

The present invention aims to overcome all these drawbacks, by supplying a device which is easy to manipulate, while reducing errors of use to a minimum and retaining a relatively simple structure which is inexpensive to manufacture.

The device that it relates to comprises, in a manner known per se:
- a container containing the product to be sprayed or to be injected,
- a plunger placed in this container and blocking off the latter, said piston being axially moveable with respect to the container, in a reference direction, allowing the product to be propelled distally from the container,
- a casing designed to accommodate and axially secure the container,
- a pusher assembled with the casing, moveable with respect to the latter, designed to come into axial abutment against the container or the plunger, and to move said plunger in the reference direction,
- means for controlling the length of travel of the pusher with respect to the casing, these means being designed to divide this travel into a first travel portion and a second travel portion, determining the respective delivery of the first and second doses.

According to one embodiment of the invention:
- the casing or the pusher comprises at least one tab which can be moved radially between a first normal or unstressed radial position, in which the tab provides no obstacle to the movement of the pusher with respect to the casing, and a second, stressed and flexed, radial position, in which the tab provides an obstacle to this movement, this tab comprising a pressing region and a nonpressing region;
- the pusher or the casing, respectively, comprises at least one projection comprising a ramp, against which said pressing region of the tab comes to bear during the movement of the pusher with respect to the casing in the direction allowing the product to be injected or sprayed, which brings said tab into said second radial position, then opposite which comes said nonpressing region of the tab, which allows said tab to return to said first radial position; the pusher or the casing, respectively, further comprises at least one stop against which the tab presses when it is brought into said second radial position by said projection, this pressure occurring just before said projection comes opposite said nonpressing region,
- the device being designed such that the release of the force exerted on the pusher, which allows this pusher to move with respect to the casing, makes it possible to free the pressure of the tab against said stop and therefore allow said tab to return to said first radial position, said projection then coming opposite said nonpressing region, this return of said tab to said first radial position making it possible to free the movement of the pusher for a following portion of travel, for the purpose of spraying or injecting a following dose of the product.

According to the present invention, the casing and the pusher are designed to be axially moveable one with respect to the other, in a direction of pressure, causing the plunger to move in the reference direction.

According to the present invention, in general, the control means comprise:
- at least one tab arranged on the pusher or the casing, able to move radially between a first, unstressed, radial position in which said tab does not block the axial movement of the pusher, and a stressed, flexed, second position in which said tab halts the axial movement of the pusher, said tab at its free end comprising a pressing region or element designed to contribute both to the halting of the axial movement of the pusher and to the flexing of the tab under the effect of the axial movement of the pusher,
- at least one ramp cooperating with said tab from an end known as the initial end to an end known as the final end and arranged respectively on the casing or on the pusher, against which the pressing region or element of said tab bears in the direction of pressure of said pusher, said ramp being designed to bring said tab from its normal first position to its flexed second position,
- at least one stop cooperating with the pressing region or element of the tab, arranged respectively on the casing or the pusher, respectively beyond or before the final end of the ramp in the direction of pressure, against which the pressing region or element of the tab finally abuts in its flexed second position,
- at least one nonpressing region or opening which is either arranged on the tab before or beyond said pressing region or element, depending on whether said tab is arranged on the pusher or on the casing, or arranged on the casing, before the stop when the tab is arranged on the pusher and the pressing element cooperates with a hollowed ramp formed on the casing, said nonpressing region or opening being designed to allow said pressing region or element to return to its unstressed normal position from the halted and flexed position of the tab when the pressure on the pusher is released, the first portion of travel of the pusher being determined by the movement of this pusher as far as its axial stop position, following contact between the pressing region or element and the stop, and the second portion of travel being determined by the movement of the pusher beyond the axial position in which the nonpressing region or opening has accommodated the pressing regional or element.

Thus, it is enough for the user to exert a force on the pusher so as to move this pusher with respect to the casing in order to free a first dose of product, until the movement of the pusher is blocked owing to the tab abutting against said stop, then to release this force in order to free this blockage and to make it possible, by a new force on the pusher, to deliver the second or following dose of product.

The handling of the device according to the invention therefore does not involve any withdrawal or removal of the stop means nor axial rotation of the pusher with respect to the casing, and is therefore particularly easy. The operation of the device eliminates virtually any risk of error of use, and the design of this device is simpler than that of a device according to the prior art.

Said nonpressing region of the tab may in particular be formed by a window made in the tab set back from the end of this tab, said pressing region being formed by the region of this tab connecting this end of the tab and this window.

Preferably, the device comprises at least two tabs, two projections and two stop regions, which are diametrically opposed, which makes the operation of the device more reliable.

Advantageously, the casing and the pusher comprise means making it possible to form at least one "hard point" having to be crossed at the start of delivering a dose. These means make it possible to prevent any unintentional spraying or injection of a dose, and therefore to make the use of the device even more reliable. These means may especially consist of at least one lug projecting laterally from a tab as mentioned above and of at least one boss made in a corresponding location of the casing or the pusher.

For it to be properly understood, the invention is again described below with reference to the appended schematic drawing showing, by way of nonlimiting example, four possible embodiments of the device to which it relates.

FIG. 1 is a perspective view thereof according to a first embodiment;

FIG. 2 is a view thereof similar to FIG. 1, in axial section;

FIGS. 9 and 10 are views thereof in axial section of the device according to the invention according to two variants of the first embodiment, respectively;

FIG. 11 is a view thereof in axial section over a sector, of a device according to the second embodiment of the invention;

FIGS. 12 to 15 are partial views thereof in axial half-section, respectively at the start of injecting a first dose, at the end of injecting this first dose, at the start of injecting the second dose and at the end of injecting this second dose, according to the second embodiment

FIG. 18 is a front-on view of a device according to a third embodiment of the present invention;

FIG. 19 is a perspective view of the casing of the device according to FIG. 18;

FIG. 20 is a perspective view of the pusher of the device according to FIG. 18;

FIG. 21 is an enlarged view, laid out flat, of the ramp belonging to the casing according to FIG. 19;

FIGS. 25 to 30 show, in axial half-section, various stages in the operation of the pusher with respect to the casing, namely, respectively:

Figure 3:
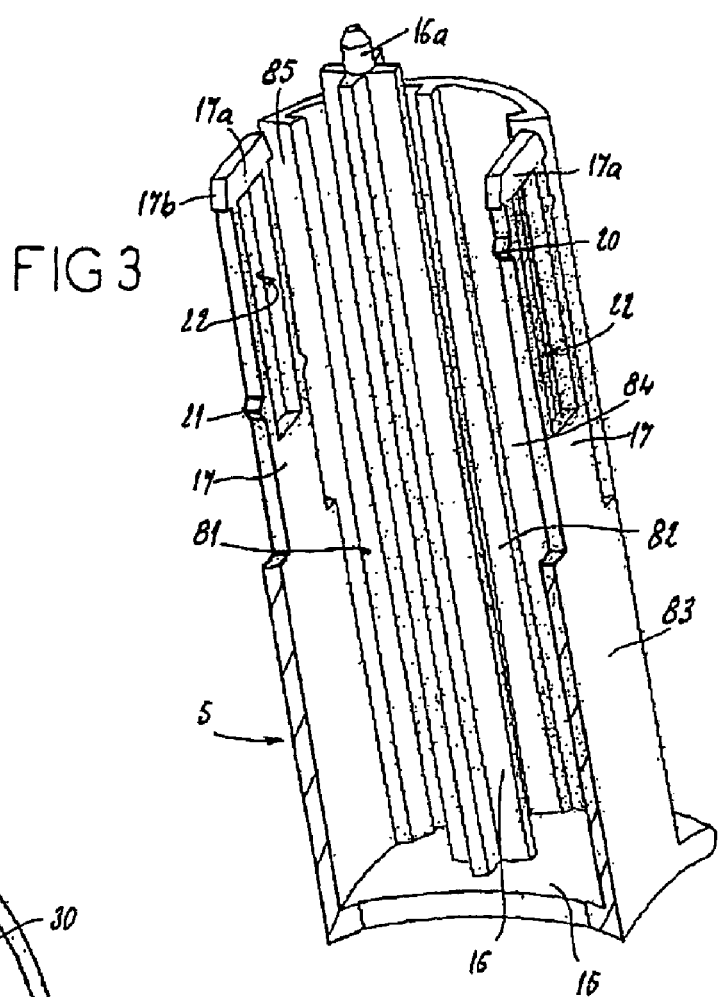
FIG. 3 is a view in partial section of the pusher which it comprises.

initial position, prior to delivery of the first dose; cf. FIG. 25;

flexing of the tab, the tongue remaining in a normal position; cf. FIG. 26;

flexing of the tab and of the tongue; cf. FIG. 27;

escape of the tab from the ramp, with flexing of the tongue; cf. FIG. 28;

continued movement of the tab, the tongue escaping from the ramp, to deliver the second dose; cf. FIG. 29;

continued movement of the tab and of the tongue, beyond the ramp, cf. FIG. 30;

intermediate position, prior to delivery of the second dose.

FIGS. 1 to 8 show a nasal spray device 1 according to a first embodiment of the invention making it possible to deliver two preset doses of a product of interest, in liquid form, one for each nostril.

This device 1 comprises a syringe body 2, a spray nozzle 3, a plunger 4, a pusher 5, a casing 6 and a protective lid 7.

The syringe body 2 is of conventional type, for example made of glass, with a proximal collar 10 and a distal flow conduit 80.

The nozzle 3 is fitted onto the distal end of the syringe body 2. It forms a spray head 11 making it possible to spray the product contained in the syringe body 2, and comprises a proximal collar 12. Since such a nozzle 3 is known per se, it is not described further in detail.

The plunger 4 is also of conventional type, being a syringe plunger.

As is shown more particularly in FIGS. 2 and 3, the pusher 5 has a generally hollow cylindrical shape, closed by a proximal bottom 15, and comprises an axial rod 16 secured to this bottom 15, accommodating the plunger 4 at its distal end by virtue of a stud 16*a* which it comprises. The wall 83 of the pusher 5 is stiffened by longitudinal internal ribs 81 and 82 parallel to the rod 16.

The pusher 5 also comprises, in the example shown, four cuts 84, 85 made longitudinally from its distal end, defining two diametrically opposed moveable tabs 17. The whole pusher 5 is made from a slightly flexible common plastic, the radial or tangential mobility of the tabs 17 resulting from the flexibility of this material. This flexibility provides the mobility of the tabs 17 between a first, undeformed, inner, unstressed, radial normal position, shown in FIGS. 2, 3, 5, 7 and 8, and a second, stressed, outer, flexed, radial position, shown in FIG. 6, in which these tabs 17 are elastically deformed.

Each tab 17 has a distal head or pressing region 17a with projecting edges 17b, forming, with a complementary means comprised in the casing 6, that is a boss 38 in the example shown, snap-fastening means making it possible to prevent the separation of the pusher 5 from the casing 6 after engagement of the pusher in the casing, as will become apparent further on.

The tabs 17 further comprise two pairs of lugs 20, 21 projecting laterally, located, from one tab to the other, at two different heights. These lugs 20, 21 define, with the corresponding bosses 38 made in the casing 6, "hard points" having to be crossed at the start of spraying a dose, as will also be explained further on.

Each tab 17 also comprises a window or nonpressing region 22 made through it, set back from a pressing region 17a; this window stretches axially over a preset length.

Figure 4:
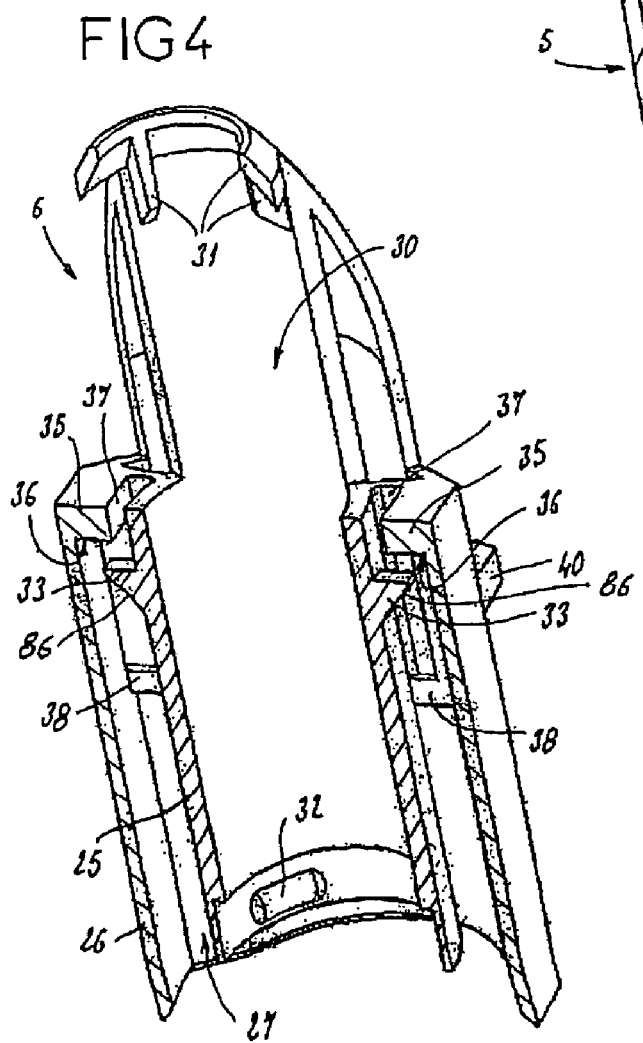
FIG. 4 is a view in axial section of the casing which it comprises.

As shown in FIGS. 2 and 4, the casing 6 comprises two walls 25, 26 joined together at the distal end of this casing, these walls 25, 26 defining between them a space 27 in which the pusher 5 is designed to be engaged so that it can slide.

The inner wall 25 defines a housing 30 for accommodating and axially securing the syringe body 2 and the spray nozzle 3, the casing 6 comprising distal tabs 31 which make it possible to center the nozzle 3 and the distal end of the syringe body 2, together with proximal bosses 32 for snap-fastening the collar 10 of the syringe body 2.

This inner wall 25 also comprises, in the example shown, two projections 33 each comprising an oblique ramp facing toward the distal end of the device 1 and diametrically opposed, projecting from its outer face, these projections 33 being designed to cooperate with the tabs 17 of the pusher 5, as will become apparent further on. These projections also have a shape tailored to penetrate freely and slide with respect to a window 22, as described hereinbelow.

Figure 17:
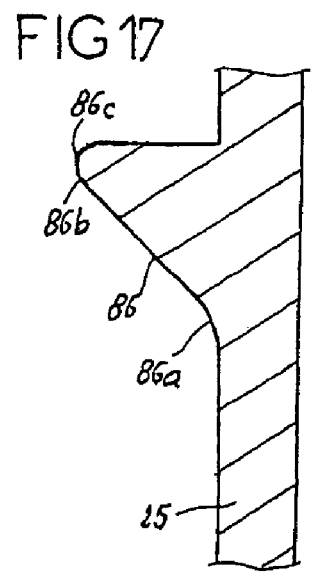
FIG. 17 shows, in an enlarged view, a detail regarding the ramp belonging to the casing of the device according to the first embodiment (FIGS. 1 to 8) of the invention.

As can be seen more clearly in FIG. 17, the ramps 86 have anterior edges 86 c (those facing toward the tabs 17) that are rounded, and shaped to be encountered by the tabs 17 only at the end of the spraying or injection of the first dose. This then prevents friction from being generated at the start of the spraying or injection of the first dose, when the pusher speed is low.

The outer wall 26 comprises two returns 35 forming, inside said space 27 and at a preset distance from the projections 33, internal stops 36 against which the distal heads 17a of the tabs 17 may respectively abut, as will also be explained further on.

These returns 35 also comprise two openings 37 which allow the tabs 17 to pass therethrough by sliding in axial translation.

The outer wall 26 further comprises the two inner bosses 38, beyond which the heads 17a of the tabs 17 snap-fasten via their projecting edges 17b in order to prevent the separation of the pusher 5 from the casing 6, and with which the lugs 20, 21 cooperate in order to form the aforementioned hard points.

The outer wall 26 also comprises, in the example shown, two diametrically opposed outer tabs 40 projecting from its outer face, serving to support two fingers of the user when exerting, on the casing 6, a force opposing the pressure exerted on the bottom of the pusher 5 by another finger of the user.

As for the lid 7, it has a transverse end wall 45 and a peripheral wall 46 which allows it to cover the part of the nozzle 3 that extends beyond the casing 6.

Figure 5:
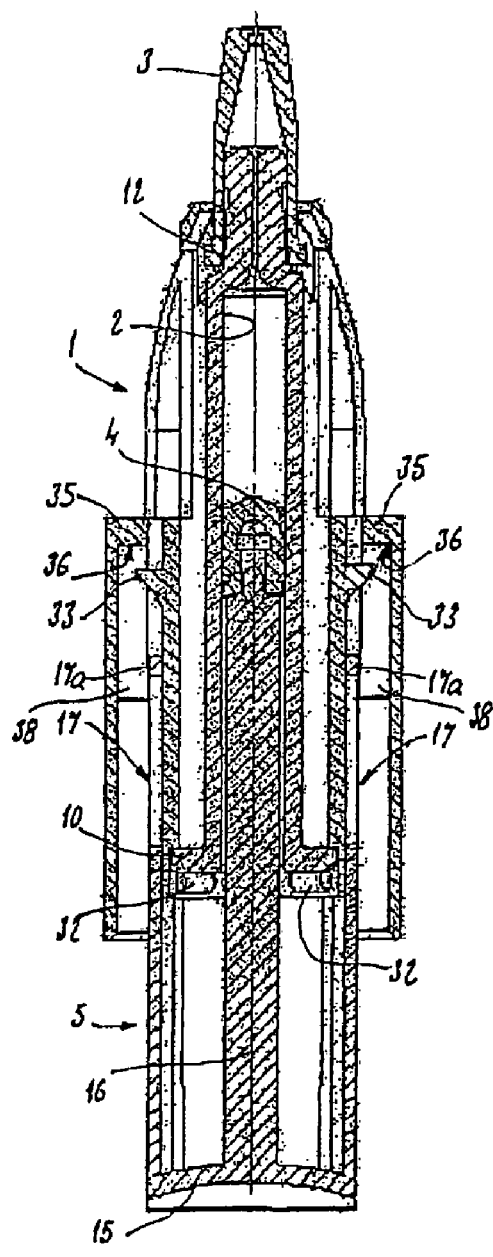
FIGS. 5 to 8 are views thereof in axial section of the device according to the first embodiment, respectively at the start of injecting a first dose, at the end of injecting this first dose, at the start of injecting the second dose and at the end of injecting this second dose.

FIG. 5 shows the device 1 at the start of the phase of spraying a first dose of product. Opposing forces are exerted on the pusher 5 and on the outer tabs 40 in order to make the aforementioned lug 20 of a tab 17 cross the corresponding boss 38 then to make the pusher 5 slide with respect to the casing 6, thus spraying the first dose.

During this movement, the heads or pressing regions 17a of the tabs 17 come against the ramps 86 of the projections 33, respectively, which moves these tabs 17 toward their abovementioned second, radially outer positions through the sliding of each of the heads 17a from an end known as the initial end 86a to an end known as the final end 86b of a ramp 86; cf. FIG. 17.

Figure 6:
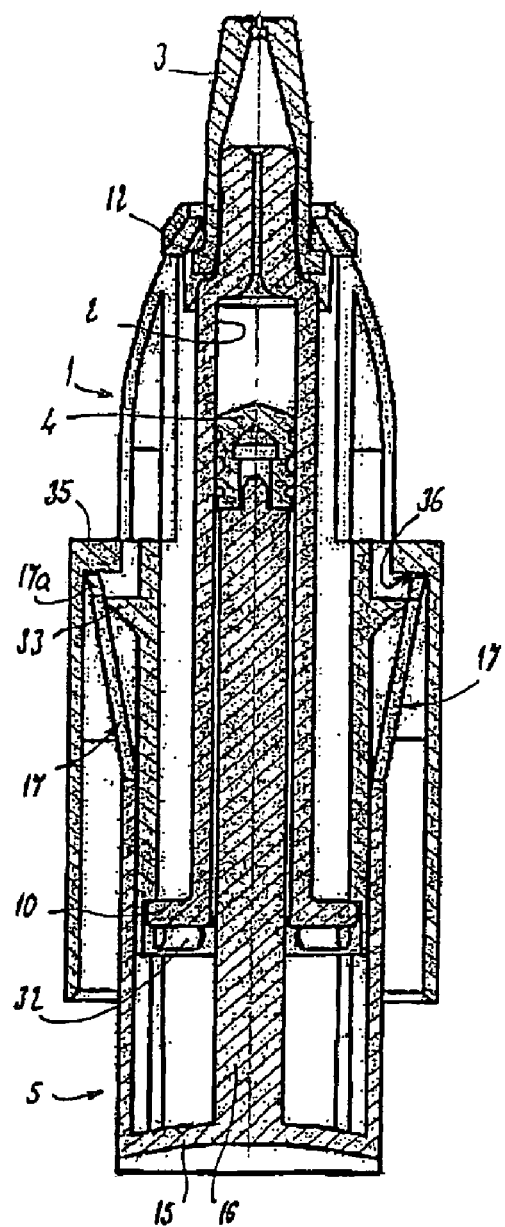

The continuation of the movement of the pusher 5 brings the heads 17a of the tabs 17 into abutment against the stops 36, as shown in FIG. 6, the distance between each stop 36 and each corresponding projection 33 being such that this abutment occurs just before the projection 33 arrives completely opposite the window 22.

The abutment of the tabs 17 against the stops 36 keeps the tabs 17 in said second, outer radial position when the projections 33 are completely opposite the respective windows 22, under the effect of the pressure, the sliding of the pusher 5 remaining blocked with respect to the casing 6, thus marking the end, of the spraying of the first dose.

Figure 7:
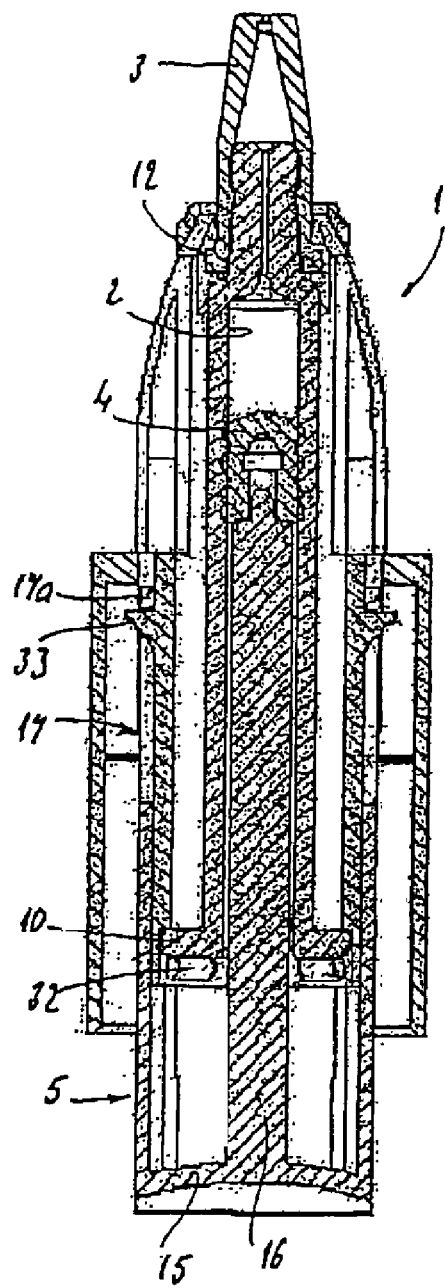
Figure 8:
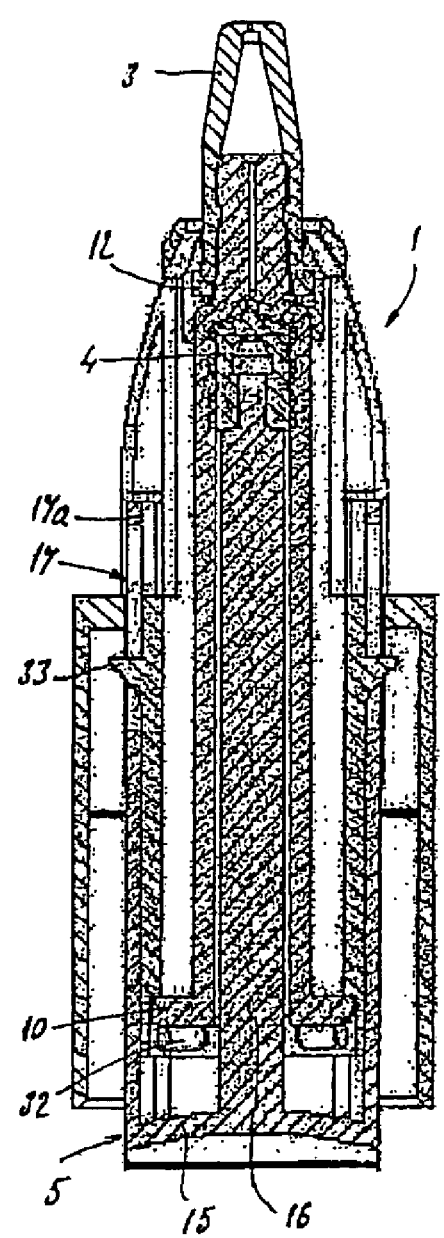

Release of the pressure exerted on the pusher 5 and therefore on the outer tabs 40 elastically frees this pressing of the heads 17a against the stops 36 and consequently allows the tabs 17 to return to their first inner radial position, as shown in FIG. 7.

Pressure may then be exerted again on the pusher 5 with an opposing force on the outer tabs 40 in order to start spraying the second dose. The lug 21 is then just below the corresponding boss 38, such that there is a second hard point having to be crossed in order to start this second spraying. Once this hard point is crossed, the second spraying may take place, the tabs 17 sliding through the openings 37 and the projections 33 sliding through the windows 22, to the end-of-spraying position shown in FIG. 8.

FIGS. 9 and 10 show a device 1 very similar to that which has just been described. The elements already described with reference to FIGS. 1 to 8, which are found again in this device and which are functionally identical or equivalent, are denoted by the same numerical references and will not be described again.

In the case of FIG. 9, the device 1 comprises a container 50 of the carpule type, with a proximal bottom 51 and a distal collar 52, a plunger 53 having a thinned central region, a hollow needle 54 suitable for piercing this thinned central region, and a rod 55 held by a spray nozzle 3 mounted on the casing 6, this rod 55 comprising the needle 54 and forming a flow conduit 56 for the product.

In practice, the central rod 16 of the pusher 5 bears against the bottom 51 of the container 50, which moves the container 50 and the plunger 53 until the needle 54 pierces the thinned central region of the plunger 53, thus allowing the liquid product of interest to flow.

In the case of FIG. 10, the device 1 comprises a container 50 identical to that of the device shown in FIG. 9 and a rod 55 similar to that comprised in this device, but without a needle 54. The plunger 60 then comprises an axial recess 61, opening out in its distal face and made on one side of this plunger 60, this recess 61 thus defining a side wall portion 60a of the plunger 60 having flexibility in the radial direction of this plunger. This wall 60*a* moves aside under the pressure of the product resulting from the pressing of the rod 55 against the plunger 60 following the movement of the container 50 with respect to the rod 55, thus freeing the flow of the product.

FIG. 11 shows a device 1 similar to that described with reference to FIGS. 1 to 8, according to a second embodiment of the invention. The tabs 17 are made on the casing 6 and the projections 33 and the stops 36 are made on the pusher 5. In this case also, the elements already described with reference to FIGS. 1 to 8, which are found in this device and which are structural and/or functionally identical or equivalent, are denoted by the same numerical references and will not be described again.

In this case, the pusher 5 comprises an inner wall 70 in which are formed the stops 36, and an outer wall 71, defining between them the openings 37. The wall 71 comprises the projections 33, each comprising a ramp 86, and extends beyond these projections 33, this wall 71 being engaged in the space 27 defined between an inner wall 25 of the casing 6 and an outer wall 26 of this same casing; connecting the tabs 40 together.

The tabs 17 are formed by cuts made on each side in said inner wall 25.

In a manner similar to that which has been described above, when spraying the first dose (cf. FIG. 12), the movement of the pusher 5 with respect to the casing 6 causes the projections 33 to move the tabs 17, and more particularly the heads 17*a*, with respect to the ramps 86, toward said second radial position (in this case, inner position) until these tabs 17 abut against the stops 36 (cf. FIG. 13); following release of the force exerted on the pusher 5, the tabs 17 return to said first radial position (cf. FIG. 14), which makes it possible to continue spraying the second dose, the tabs 17 engaging in the openings 37, and the projections 33 in the windows 22, until the end of this spraying (cf. FIG. 15).

The means for controlling the length of travel of the pusher 5 with respect to the casing 6, which are common to the first two embodiments of the present invention, those according to FIGS. 1 and 11 respectively, therefore comprise:

- at least one tab (17) arranged on the pusher (5) or the casing (6), able to move between a first, unstressed, normal position in which said tab does not block the axial movement of the pusher, and a stressed, flexed, second position in which said tab halts the axial movement of the pusher, said tab at its free end comprising a pressing region or element (17*a*) designed to contribute both to the halting of the axial movement of the pusher (5) and to the flexing of the tab (17) under the effect of the axial movement of the pusher,
- at least one ramp (86) cooperating with said tab from an initial end (86*a*) to a final end (86*b*) and arranged respectively on the casing (6) or on the pusher (5), against which the pressing region or element (17*a*) of said tab (17) bears in the direction of pressure of said pusher (5), said ramp being designed to bring said tab from its normal first position to its flexed second position,
- at least one stop (36) cooperating with the pressing region or element (17*a*) of the tab (17), arranged respectively on the casing (6) or the pusher (5), respectively beyond or before the final end (86*b*) of the ramp (86) in the direction of pressure, against which the pressing region or element (17*a*) of the tab (17) finally abuts in its flexed second position,
- at least one nonpressing region or opening (22) which is arranged on the tab (17) before or beyond said pressing region or element (17*a*), depending on whether said tab is arranged on the pusher (5) or on the casing (6), said nonpressing region or opening (22) being designed to allow said pressing region or element (17*a*) to return to its unstressed normal position from the halted and flexed position of the tab (17) when the pressure on the pusher (5) is released,
- the first portion of travel of the pusher (5) being determined by the movement of this pusher as far as its axial stop position, following contact between the pressing region or element (17*a*) and the stop (36), and the second portion of travel being determined by the movement of the pusher beyond the axial position in which the nonpressing region or opening (22) has accommodated the pressing region or element (17*a*).

Figure 16:
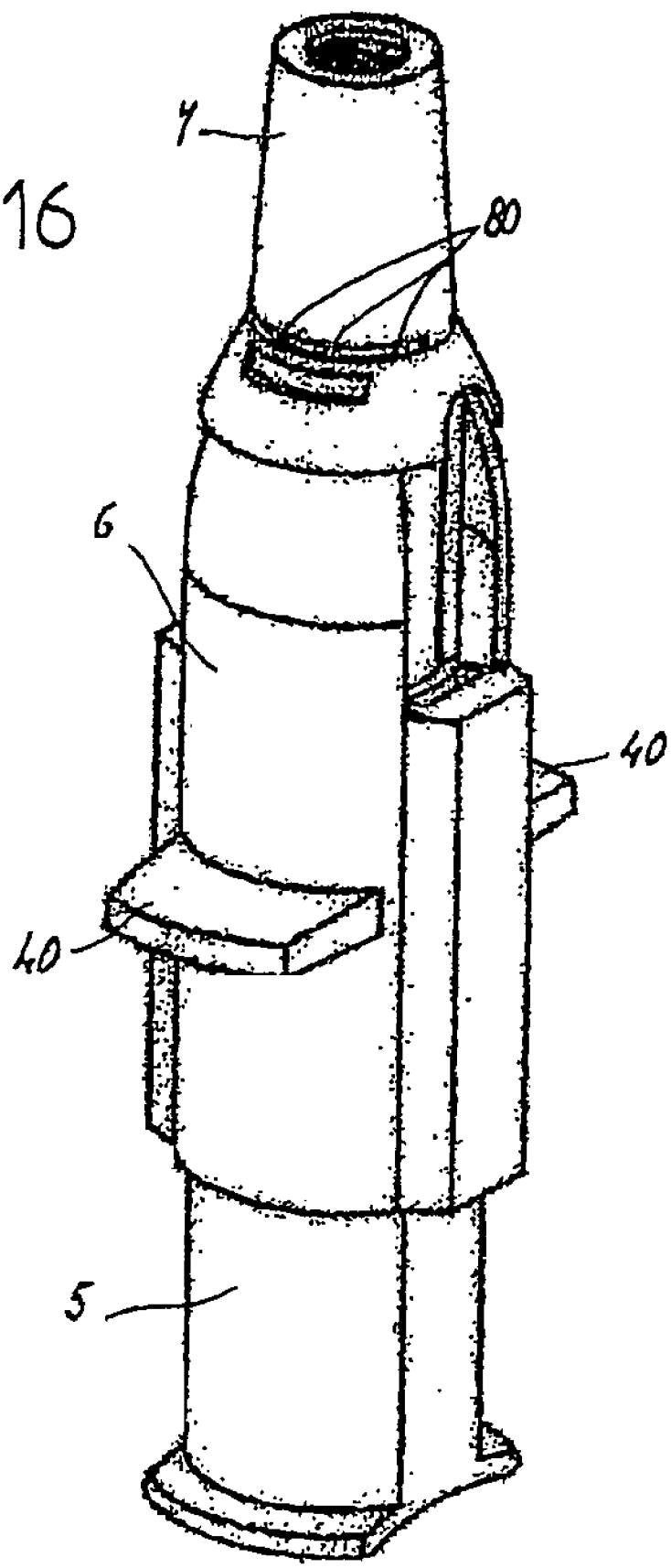
FIG. 16 is a view of a third variant of the first embodiment of the invention.
Figure 23:
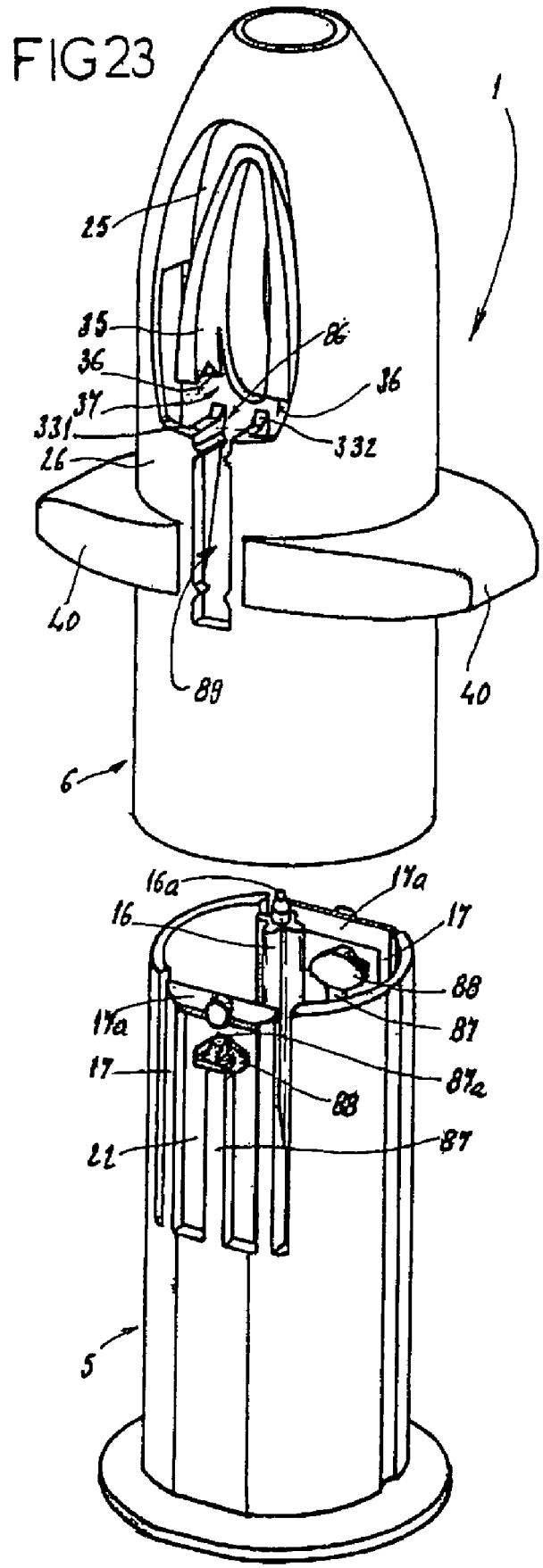
FIG. 23 shows, in perspective, and separately, the casing and the pusher of the device according to FIG. 22.
Figure 22:
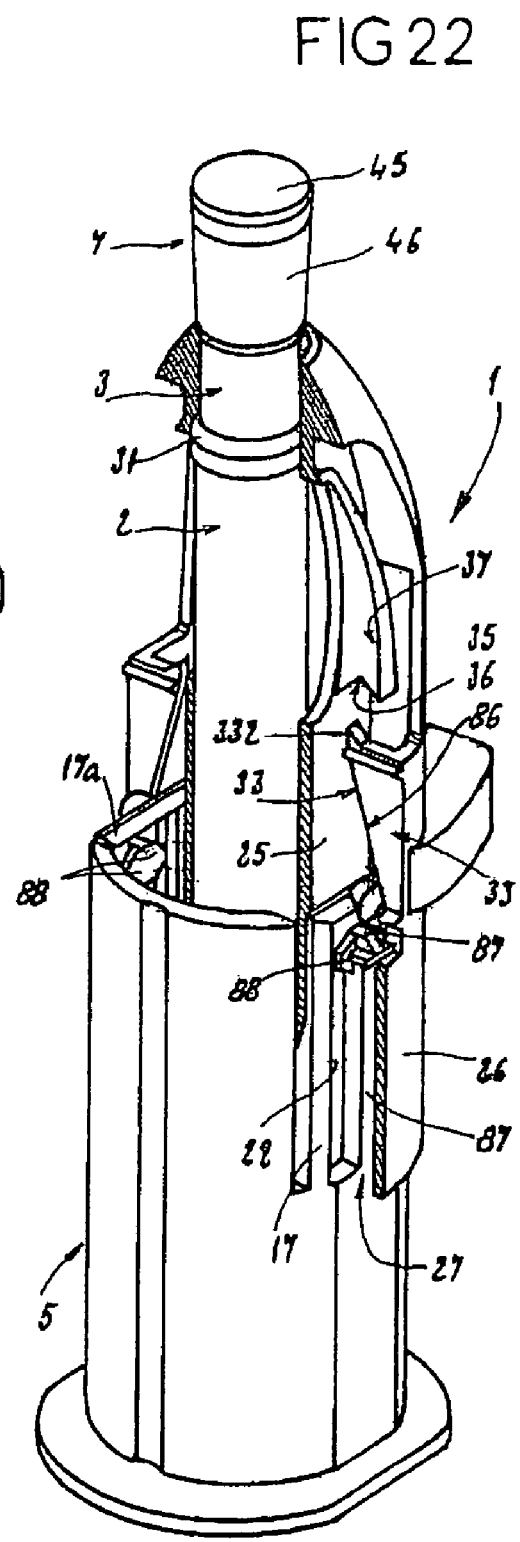
FIG. 22 shows, in perspective, with partial section, a device according to a fourth embodiment of the invention.

FIG. 16 shows a device 1 similar to the first embodiment, except that it comprises a lid 7 connected to the casing 6 by breakable bridges 80. These bridges 80 make it possible to force the user to have a deliberate action of use and to prevent this use being too easy for children.

A third embodiment of a device according to the invention, characterized in particular in that the flexed second position of the tabs 17 is obtained by tangential stress, is now described with reference to FIGS. 18 to 20.

According to this third embodiment of the present invention, as was the case with the first embodiment previously described, the tabs 17 are arranged on, the pusher 5, while the ramp 86 is arranged on the casing 6, in the form of a continuous groove passing through the wall of said casing.

The nonpressing opening 22, belonging to the through groove, is arranged on the casing 6, before the stop 36, also belonging to said through groove, when the tab 17 is arranged on the pusher 5 (as already indicated) and the pressing element 17*a* specified hereinbelow cooperates with the hollow ramp 86 formed on the casing 6.

Each tab 17 arranged on the pusher 5 at its free end comprises a stud 17*a* forming a pressing element or region extending transversely toward the casing 6. A V-shaped cut 84, anterior with respect to the tab 17, allows the latter to deflect tangentially from its normal first position to its flexed second position. The ramp 86 arranged on the casing 6 is arranged in a hollow, or such that it passes through, so as to accommodate the stud 17*a* and extends more or less obliquely (compare FIG. 21) in the wall of the casing 6, from the initial end 86*a* to the final end 86*b*. The stop 36 discussed in the previous forms of embodiment of the invention cooperates with the stud 17*a*, it is arranged on the casing 6 beyond the final end 86*b* of the ramp 86 and is determined by the joining at an angle, but with continuity, of the ramp 86 with ramp return 90, of inverse slope with respect to the actual ramp 86 proper. The nonpressing region or opening 22 discussed earlier is arranged in a hollow on the casing 6, before the abovementioned stop 36, in continuity with the ramp 86 and the ramp return 90; this non-pressing region 22 is designed to accommodate the stud 17*a* when the tab 17 returns to its normal position from its halted and flexed position. Further, an axial slot 91 extends in continuity from the previously described nonpressing region 22 but beyond the latter. The axial slot 91 in the casing 6 opens out freely into a through opening 92 of the casing 6, forming a window through the outer wall of said casing; it being understood that, according to this third embodiment of the invention, the second portion of travel of the pusher 5 is determined by the abutment of the plunger against the wall of the container 2.

Before the initial end 86*a* of the ramp 86, and continuous therewith, a housing 93 in which to park the stud 17 is formed. The snap-fitting of the stud 17*a* into the housing 93 allows definitive assembly of the pusher 5 and of the casing 6.

Beyond the nonpressing region or opening 22, and in continuity therewith, a housing 94 for parking the stud 17a is formed, like the housing 93, in the outer wall of the casing 6.

The third embodiment of the invention already described gives greater robustness and a smaller axial size. This embodiment also guarantees effective halting of the pusher with respect to the casing between the two portions of the travel of said pusher, and therefore before the second dose of the product of interest is delivered.

A fourth and final embodiment of the present invention, which is like the first or second embodiment already described, is now described with reference to FIGS. 22 to 30.

At least one tongue 87, separate from or independent of the tab 17, is arranged, as the case may be, on either the pusher 5 or the casing 6, depending on whether the tab 17 is itself arranged on the pusher 5 or the casing 6, respectively. This tongue 87 can move between an unstressed normal first position in which said tongue does not in general impede the axial movement of the pusher during the two successive portions of travel thereof, and a stressed flexed second position in which said tongue 87 plays a part in returning the pusher 5, in the opposite direction to the pressure, and does so in order to allow the tab or tabs 17 to return to their normal position from their flexed halted position. As shown in perspective in FIG. 23, but more explicitly in FIGS. 25 to 30, the ramp 86 and the free end 87a of the tongue 87 are designed to cooperate with one another so that during the first portion of travel of the pusher, for example at the end thereof, the tongue 87 finds itself flexed (compare FIG. 27), and during the second portion of travel of the pusher the tongue 87 escapes the ramp 86 and returns to its normal position (compare FIGS. 29 and 30). The unstressed normal first position of the tongue 87 is shown in FIG. 25, while a stressed flexed second position is shown in FIGS. 26 to 28.

According to FIGS. 22 to 30, the flexed second position of the tongue 87 is obtained by radial stress when the flexed second position of the tabs 17 is itself obtained by radial stress also. It must be understood that, in a way which has not been depicted, this flexed second position of the tongue 87 could be obtained by tangential stress, while the flexed second position of the tabs 17 would itself be obtained by tangential stress.

Each tab 17, arranged, as the case may be, on the pusher 5 or the casing 6, comprises a nonpressing window 22 of overall rectangular shape, at the center of which the tongue 87 extends parallel to the axis of the device. As in the other embodiments of the invention, the ramp 86 belongs to a projection 33 arranged, as the case may be, on the casing 6 or on the pusher 5, which ramp is designed to pass freely through the window 22. The stop 36 is arranged, on the casing 6 or the pusher 5, as the case may be, such that when each tab 17 is in the flexed second position, the projection 33 comes to face the window 22 then penetrates through this window when the pressure on the pusher 5 is released, thus causing each tab 17 to return to its first position.

More specifically, each tongue 87 is arranged at the center of the window 22 with its free end, 87a remaining before the head 17a or pressing region of the corresponding tab. The free end 87a comprises two ears 88 for pressing against the ramp 86. The latter comprises two parallel flanges 331 and 332 arranged on each side of a slot 89, which allows the tongue 87 free passage in translation. Each ear 88 is designed to come into contact with a ramp portion 86 defined by a flange 331 or 332 and to do so in the direction of pressure of the pusher 5; beyond the first portion of travel of the pusher 5, each ear 88 escapes from the corresponding ramp portion or flanges 331 or 332 so that the tongue 87 returns to the normal position.

Figure 24:
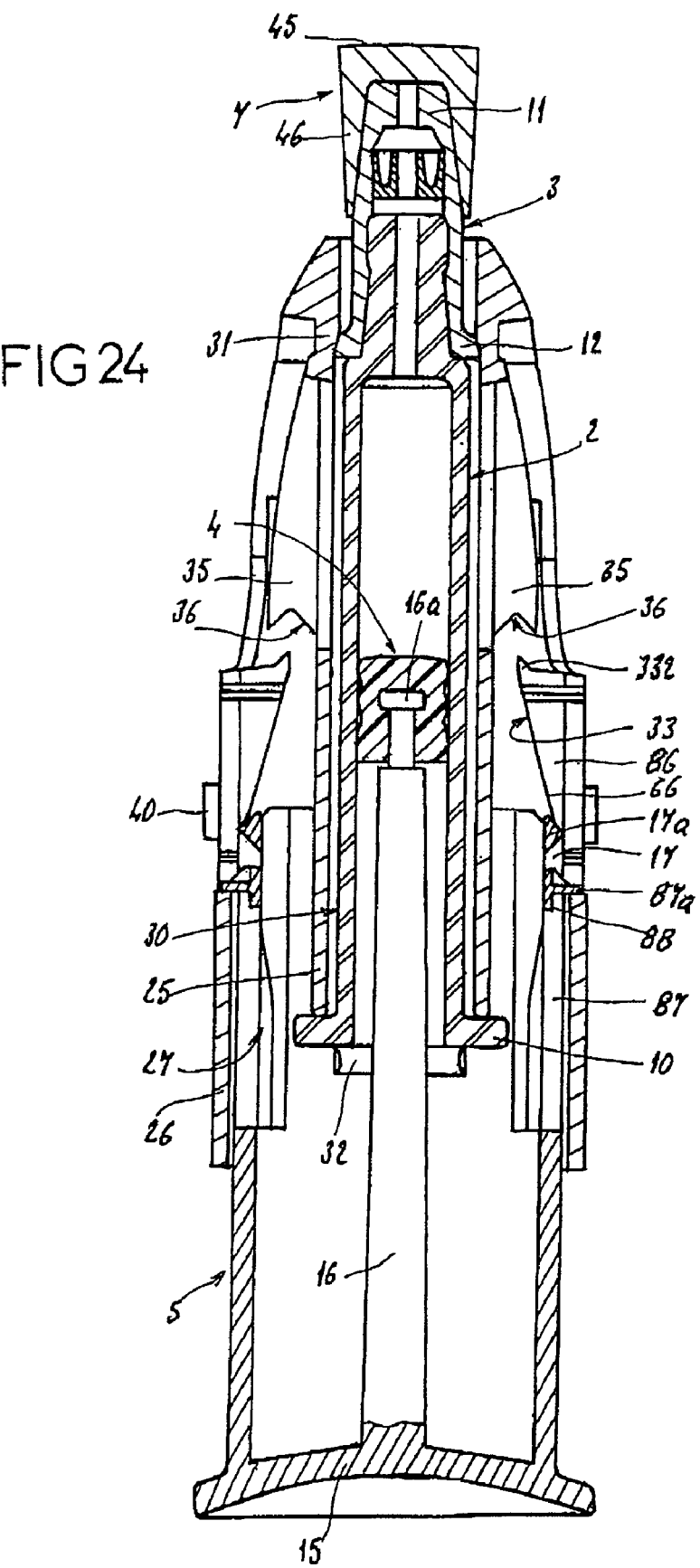
FIG. 24 shows a view in axial section of the device according to FIG. 22.

In the initial position of the pusher 5 with respect to the casing 6, which position is shown in FIG. 24, the tab 17 and the tongue 87 are in their normal, radial, and unstressed, position.

According to FIG. 26, by pressure on the pusher 5, the movement of the head 17a of the tab 17 causes this tab to flex without in any way, to start with, causing the corresponding tongue 87 to flex, such flexing occurs at the end of the travel of the head 17a.

According to FIG. 27, by continuing the movement of the pusher 5, the tab 17 is fully flexed whereas the ears 88, in contact with the ramp 33 and more specifically with the flanges 331 and 332, respectively, flexing the corresponding tongue 87, by virtue of the nonpressing region or opening 22, by continuing the pressure of the pusher 5, the tab 17 escapes the ramp 86, or projection 33, the corresponding tongue 87 remaining flexed, the flexed tongue 87 exerts on the ramp 86 an antagonistic pressure that contributes to the return of the pusher 5, in the opposite direction to the pressure, when this pressure is released. In consequence, the tongue 87 returns to a flexed intermediate position; cf. FIG. 28.

Starting out from the relative position of the casing and of the pusher which have been shown, in FIG. 28, by resuming the pressure on the pusher 5, the free end 87a of the tongue 87 in contact with the ramp 86 immediately escapes the latter (cf. FIG. 29) so that the pusher 5 can be pushed beyond the relative position shown by FIG. 28, in order to deliver the second dose of the product of interest; cf. FIG. 30.

As is apparent from the above, the invention provides a decisive improvement to the prior art, by providing a device which is easy to manipulate, while reducing errors of use to a minimum and retaining a structure which is relatively simple and inexpensive to manufacture.

It goes without saying that the invention is not limited to the embodiment described above by way of example but that, on the contrary, it covers all the variant embodiments that fall with respect to the field of protection defined by the claims appended hereto. The syringe body 2 and the spray nozzle 3 may especially be manufactured as a single part.

The invention claimed is:

1. A spray or injection device for spraying or injecting a product of interest, in liquid form, the device being configured to deliver at least a first and a second preset dose of said product in succession, said device extending along a reference axis from a distal end to a proximal end, the device comprising:

an axially elongate container containing said product;

a plunger disposed in and blocking off the container, the plunger being axially moveable with respect to the container, in the reference direction, and allowing said product to be propelled distally from the container;

a casing configured to accommodate and axially secure said container;

a pusher assembled with the casing, the pusher being moveable with respect to the casing, and configured to come into axial and proximal abutment against the container or the plunger, and to move said plunger in the reference direction;

means for controlling the length of travel of the pusher with respect to the casing, the controlling means being configured divide the length of travel of the pusher into a first travel portion and a second travel portion, and determine the respective delivery of the first and second doses, the casing and the pusher being configured to be axially moveable one with respect to the other in a pushing direction, and generate the movement of the plunger in the reference direction, the control means comprising at least one tab arranged on the pusher or the casing, and configured to move between a first, unstressed, normal position in which said tab does not block the axial movement of the pusher, and a stressed, flexed, second position in which said tab halts the axial movement of the pusher, said tab at a free end comprising a pressing region or element configured to contribute both to the halting of the axial movement of the pusher and to the flexing of the tab under the effect of the axial movement of the pusher;

at least one ramp cooperating with said tab from an initial end (86*a*) to a final end, and arranged respectively on the casing or on the pusher, against which the pressing region or the element of said tab bears in the direction of pressure of said pusher, said ramp being configured to bring said tab from the normal first position to the flexed second position;

at least one stop cooperating with the pressing region or element of the tab, and arranged respectively on the casing or the pusher, respectively, beyond or before the final end of the ramp in the direction of pressure, against which the pressing region or element of the tab abuts in the flexed second position; and at least one nonpressing region or opening which is either arranged on the tab before or beyond said pressing region or element, depending on whether said tab is arranged on the pusher or on the casing, or arranged on the casing before the stop when the tab is arranged on the pusher and the pressing element cooperates with a hollowed ramp formed on the casing, said nonpressing region or opening being configured to allow said pressing region or element to return to the first, unstressed, normal position from the stressed, flexed second position of the tab when the pressure on the pusher is released;

wherein the first portion of travel of the pusher is determined by the movement of the pusher as far as the axial stop position, following contact between the pressing region or element and the stop, and the second portion of travel being is determined by the movement of the pusher beyond the axial position in which the nonpressing region or opening has accommodated the pressing region or element.

2. The device as claimed in claim 1, wherein the flexed second position of the tab is obtained by radial stress.

3. The device as claimed in claim 2, wherein the tab arranged on the pusher or the casing comprises a nonpressing window set back with respect to said pressing region or element wherein the ramp is included in a projection arranged respectively on the casing or the pusher and configured to pass freely through said window, and wherein, if the stop is arranged in the flexed second position of said tab, the projection faces the window of the tab, and penetrates through said window when the pressure on the pusher is released, causing said tab to return to the first position.

4. The device as claimed in claim 1, wherein the flexed second position of the tab is obtained by tangential stress.

5. The device as claimed in claim 4, wherein the tab is arranged on the pusher, and disposed at the free end of the tab is a stud extending transversely toward the casing, and an anterior cut disposed proximate to said tab allowing the tab to deflect tangentially from the first, normal, position to the second flexed position;

wherein the ramp is arranged on the casing, and comprises a hollow area to accommodate the stud, and extends more or less obliquely in the wall of the casing, from the initial end to the final end;

wherein the stop that cooperates with the stud arranged on the casing beyond the final end of the ramp is determined by the joint, at an angle, but with continuity, of said ramp with a ramp return;

wherein the nonpressing region or opening arranged in a hollow area on the casing before the stop is configured to accommodate the stud when the tab returns to the normal position; and wherein an axial slot extends, continuous with the nonpressing region, beyond the nonpressing region.

6. The device as claimed in claim 5, wherein the axial slot opens out freely into a through opening in the casing, and the second portion of travel of the pusher is determined by the abutment of the plunger against the wall of the container.

7. The device as claimed in claim 5, wherein, before the initial end of the ramp, and continuous with the ramp, a housing is included in which the stud is disposed, to allow definitive assembly of the pusher and of the casing.

8. The device as claimed in claim 5, wherein, beyond the nonpressing region or opening, and continuous with the nonpressing region or opening, a housing is included in which the stud is disposed.

9. The device as claimed in claim 1, further comprising at least one tongue distinct from or independent of the tab, arranged on the pusher or the casing depending on whether the tab is arranged on the pusher or on the casing, configured to move between the first unstressed normal position in which said tongue does not impede the axial movement of the pusher and the second stressed, flexed position in which said tongue contributes to returning the pusher to allow said tab to return to the first, unstressed normal position, from the second, stressed, flexed position, and wherein the ramp and the free end of the tongue are configured to cooperate with one another such that, during the first portion of travel of the pusher, the tongue is flexed, and during the second portion of travel of the pusher, the tongue escapes from the ramp and returns to the first, unstressed normal position.

10. The device as claimed in claim 9, wherein the flexed second position of the tongue is obtained by tangential stress when the flexed second position of the tab is obtained by tangential stress.

11. The device as claimed in claim 9, wherein the flexed second position of the tongue is obtained by radial stress when the flexed second position of the tab is obtained by radial stress.

12. The device as claimed in claim 11, wherein the tab arranged on the pusher or the casing comprises a nonpressing window, the ramp is included in a projection arranged respectively on the casing or on the pusher and configured pass freely through said window the stop is arranged such that, when said tab is in the second, stressed, flexed second position, the projection faces the window of the tab and penetrates through said window when the pressure on the pusher is released, causing said tab to return to the first, unstressed, normal position.

13. The device as claimed in claim 12, wherein the tongue is arranged at the center of the window, the free end of the tongue remains before the element and comprises two ears for pressing against the ramp the ramp comprises two flanges arranged one on each side of a slot allowing the tongue free passage in translation, and each ear comes into contact with a ramp portion defined by a flange in the direction of pressure of the plunger to escape from said ramp portion beyond the first portion of travel of the pusher.

* * * * *